United States Patent [19]

Busch et al.

[11] 3,957,065

[45] May 18, 1976

[54] AGENTS FOR PERMANENT WAVING OF HUMAN HAIR CONTAINING KERATEIN AND PROCESS FOR USING THE SAME

[75] Inventors: Peter Busch, Willich; Alfons Sturm, Dusseldorf-Holthausen, both of Germany

[73] Assignee: Henkel & Cie G.m.b.H., Dusseldorf, Germany

[22] Filed: Sept. 5, 1974

[21] Appl. No.: 503,250

[30] Foreign Application Priority Data
Sept. 10, 1973 Germany............................ 2345621

[52] U.S. Cl.................................... 132/7; 8/127.51;
8/127.6; 424/DIG. 2; 424/70; 424/71;
424/72; 424/359
[51] Int. Cl.[2]......................................... A45D 7/04
[58] Field of Search ................. 424/70, 71, 72, 359,
424/DIG. 2; 132/7; 8/127.51, 127.6, 128

[56] References Cited

UNITED STATES PATENTS

| 2,413,983 | 1/1947 | Lustig et al. ......................... 260/112 |
| 2,434,688 | 1/1948 | Evans.................................. 8/127.6 X |
| 2,474,339 | 6/1949 | Ward et al. ........................... 252/316 |
| 2,540,494 | 2/1951 | Schwarz.............................. 424/72 X |
| 2,631,965 | 3/1953 | Schnell ................................. 424/72 |
| 3,683,939 | 8/1972 | Johnsen et al. .................... 424/71 X |

OTHER PUBLICATIONS

Neurath, *The Proteins*, Vol. IV, Academic Press, New York, (1966), pp. 318–319.

*Primary Examiner*—Stanley J. Friedman
*Assistant Examiner*—Vera C. Clarke
*Attorney, Agent, or Firm*—Hammond & Littell

[57] ABSTRACT

Process and composition for permanent waving of human hair containing hair-softeners and keratein so as to reduce damage to the hair.

12 Claims, No Drawings

AGENTS FOR PERMANENT WAVING OF HUMAN HAIR CONTAINING KERATEIN AND PROCESS FOR USING THE SAME

THE PRIOR ART

It is known to use various compositions for the permanent waving of human hair which contain hair-softening compounds, for example alkali metal carbonates, borax, alkali metal phosphates, ammonia, alkali metal sulfates or ammonium sulfate, sulfides and substituted mercaptans, such as mercaptoalkane-sulfonic acids, mercaptoalcohols, for example thioglycerin, and mercaptocarboxylic acids, for example mercaptosuccinic acid, mercaptopropionic acid, thiolactic acid, thioglycolic acid, as well as water-soluble derivatives of the last mentioned acid compounds, such as salts, esters, or amides. But of the above mentioned compounds, only thioglycolic acid and its derivatives have recently been widely used in practice. This so-called wave-treatment of the hair, causes, however, damage to the fiber substance of the hair. The damage manifests itself in a number of physical and chemical changes in the hair, among the most noticeable of which are the feel and luster of the hair, reduction in its tensile strength, and an increased swelling of the hair.

OBJECTS OF THE INVENTION

It is an object of the present invention to provide an agent composition for permanently waving hair which contains keratein and a hair-softening agent, and to provide a process for using this agent composition.

It is another object of the present invention to provide a composition and method for permanently waving hair which do not cause any substantial damage to the fibrous material of the hair.

These and further objects of the present invention will become apparent as the description thereof proceeds.

DESCRIPTION OF THE INVENTION

The invention relates to agents for the permanent waving of human hair which contain keratein so as to reduce damage to the hair. as well as to a process for utilizing these agents to permanently wave human hair.

More particularly the present invention provides a preparation for the permanent waving of hair consisting essentially of
A. from 1% to 10% by weight of keratein based upon the total weight,
B. from 3% to 10% by weight of hair-softening agent based upon the total weight, and
C. the balance up to 100% by weight of at least one ingredient selected from the group consisting of a wetting agent, a thickening agent, a dye, a sequestering agent, a perfume, a pH adjusting reagent, water and mixtures thereof.

The present invention is, in addition, directed to an improvement in the process for permanent waving hair which comprises applying a permanent waving agent containing a hair softening agent to the hair, applying an oxidizing fixing agent to the hair, at a temperature and for a time effective to permanently wave said hair, and removing said agents from the hair. The improvement consists essentially in the present of from 1% to 10% by weight of keratein, in said permanent waving agent containing a hair-softening agent.

The present invention furthermore relates to a process for the permanent waving of human hair consisting essentially of applying to said hair at a temperature ranging from about 15°C to 15°C for a time sufficient to soften said hair, an effective amount of a preparation consisting essentially of
A. from 1% to 10% by weight of keratein based upon the total weight,
B. from 3% to 10% by weight of a hair-softening agent based upon the total weight, and
C. the balance up to 100% by weight of at least one ingredient selected from the group consisting of a wetting agent, a thickening agent, a dye, a sequestering agent, a perfume, a pH adjusting reagent, water and mixtures thereof; and thereafter applying to said hair an oxidizing fixing agent.

The advantages of the process and agent composition according to the invention for the permanent waving of hair based on hair-softening compounds and containing keratein are that they do not cause any severe damage to the fiber substance of the hair. Hair which had been treated with a keratein containing waving lotion has a more lustrous appearance and feels softer to the touch than hair treated in the prior art manner without the addition of keratein. Physical and chemical tests prove convincingly the gentle treatment of the hair by the permanent waving agents according to the invention.

The keratein used in the compositions, lotion or preparations according to the invention to reduce damage to the hair is chemically a reduced keratin. It can be obtained in known manner from keratin containing material, such as hair, nails, claws, hoofs and feathers, by treatment in an alkaline medium with reducing agents capable of reducing the disulfide groups. To achieve this result the keratin materials are treated so as to remove the fats and oils. Then they are treated for several hours at room temperature in an alkaline medium, preferably at a pH range of 10 to 13, with compounds capable of reducing the disulfide groups. The resulting keratein solutions are then dehydrated.

Examples of compounds capable of reducing the disulifide groups include alkaline earth metal cyanides such as calcium cyanide, alkali metal sulfides such as sodium sulfide, alkali metal sulfites such as sodium sulfite and mercaptocarboxylic acids such as thioglycolic acid.

The resulting keratein is obtained as a water-soluble brown mass which becomes water-insoluble after prolonged storage in the air. By adding alkaline solutions which have a reducing effect on disulfide groups, the water-insoluble product again becomes water-soluble.

The method of reductive splitting of the keratin substances into the protein substance, keratein, is known according to the literature, for example David Goddard et al., *Journal of Biological Chemistry*, Vol. 106 (1934), p. 605–614. This reaction is a simple reduction of the disulfide groups to sulfhydryl groups without any further chemical change in the molecule, and is represented by the following schematic equation:

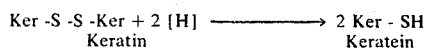

$$\text{Ker-S-S-Ker} + 2\,[H] \longrightarrow 2\,\text{Ker-SH}$$
$$\text{Keratin} \qquad\qquad\qquad\qquad \text{Keratein}$$

After prolonged standing in air, an oxidative cross-linkage of the thiol groups to produce the disulfide bridges may take place again, which crosslinking can again be reversed by adding alkaline solutions which have a reducing effect on the disulfide groups.

The compositions according to the invention for the permanent waving of hair based on hair-softening compounds and containing keratein may be utilized as a preparation in the form of a solution, a gel, a creme, a lotion, or a powder. The amount of keratein ranges from 1% to 10% by weight, preferably from 3% to 7% by weight, based on the total weight of the preparation.

Suitable examples of hair-softening compounds include alkali metal carbonates such as sodium carbonate, alkali metal phosphates, borax, ammonia, ammonium carbonate, alkali metal sulfites such as sodium sulfite, ammonium sulfite, ammonium sulfide, dithiocarbamic acid derivatives, mercaptoalkanesulfonic acid derivatives, thioglycerin, mercaptocarboxylic acid derivatives preferably mercaptoaliphatic acid derivatives such as mercaptosuccinic acid derivatives, mercaptopropionic acid derivatives, thioalkanoic acid derivatives of 2 to 6, preferably 2 to 3, carbon atoms such as thiolactic acid derivatives, thioglycolic acid derivatives which may be present in amounts known for using for hair softening. The above acid derivatives are present in the form of their water-soluble salts. Generally the amount used ranges from 3% to 10% by weight based upon the total weight. Preferred as hair-softening agents are the salts of thioglycolic acid, particularly the ammonium salt, which is used in a concentration of 3% to 10% by weight, calculated as thioglycolic acid and based upon the total composition weight.

In compositions of this type for the permanent waving of hair, the agents of the invention can contain the additive ingredients usually present in such preparations, such as thickeners, wetting agents, sequestering agents, dyes and perfume oils.

Most suitable for use as thickeners are cellulose derivatives, for example methyl cellulose, polyvinyl pyrrolidone, or polyacrylates such as poly-lower alkyl acrylates and methacrylates, as well as higher fatty alcohols together with the rest or alone. suitable wetting agents include the anionic and nonionic surface-active compounds such as, for example, higher fatty alcohol-sulfates, higher fatty alcohol lower alkylene oxide adducts-sulfates, alkyl-benzene sulfonates, condensation products of higher fatty alcohols with ethylene oxide, and cationic surface-active compounds such as cetylpyridinium chloride. Suitable sequestering agents include organic acylation products of phosphorous acid or their derivatives with at least two phosphorus atoms in the molecule, such as the alkane-1,1-diphosphonates. Another additive utilized is a pH adjustment reagent such as ammonia.

The various additives are utilized in the amounts effective for this purpose. An effective amount of a wetting agent or surface active agent added is from 0.5% to 30% by weight; and an effective amount of a thickening agent added is from 0.1% to 25% by weight, calculated in each case on the total composition. An effective amount of the dye in such preparations is from 0.1% to 0.5% by weight, based upon the total composition. An effective amount of a sequestering agent is from 0.1% to 10% by weight, and an effective amount of a perfume oil is from 0.1% to 5% by weight. An effective amount of a pH adjustment reagent is from 0.1% to 10% by weight.

Specific examples of the above additive ingredients are as follows: condensation products of higher fatty alcohol mixture having chain lengths of $C_{12}$ to $C_{18}$ with 8 to 10 mols of ethylene oxide; higher fatty alcohol mixture having chain lengths of $C_{12}$ to $C_{18}$; and higher fatty alcohol sulfate.

Generally speaking the preparation for permanent waving of the hair contains keratein, a hair-softening agent and the balance up to 100% by weight of one or more of these additive ingredients, as well as water, and mixtures thereof.

The application of the permanent waving agent preparations may be effected at temperatures between 15°C and 40°C, preferably room temperature.

After the hair permanent waving agents according to the invention are applied to the hair, the hair is treated with the usual oxidizing fixing agents, or setting agent, with which the keratein is chemically fixed onto the hair. These fixing agents, or setting agents, include, for example, 2% to 6% by weight of a hydrogen peroxide solution or a potassium bromate solution.

The following examples are merely illustrative of the present invention without being limitative in any manner thereof.

EXAMPLE 1

The keratein required for the following experiments was produced as follows:

100 gm Of poodle hair was de-oiled by boiling for 1 hour under reflux with methylene chloride. The hair was then drained off and dried. The dried hair was treated at room temperature for 5 hours with 1 liter of saturated sodium sulfide solution. Then the undissolved hair was filtered from the reaction product; and the resulting aqueous solution was concentrated to dryness. 38 gm of a water-soluble brown mass were obtained, which represented the desired keratein. A titrimetric determination with an iodine solution give 2.4% of free thiol groups.

EXAMPLE 2

50 gm of poodle hair were de-oiled using a procedure analogous to that described in Example 1 above. Then the de-oiled poodle hair was treated for 5 hours at room temperature with an aqueous solution of 30 gm thioglycolic acid, which was standardized with sodium hydroxide solution to a pH of 12. The preparation of the solution was effected analogously to that described in Example 1 wherein sodium sulfide was used. The yield was 22 gm of a water-soluble, brown mass. A titrimetric determination with an iodine solution yielded 2.5% of free thiol groups.

EXAMPLE 3

The waving tests for untreated human hair were carried out in the following manner, both with and without the addition of keratein prepared as described above.

A cold *permanent waving lotion* had the following composition:

| | |
|---|---|
| Thioglycolic acid | 60 gm |
| Ammonia | 70 gm |
| Condensation product of $C_{12}$ to $C_{18}$ fatty alcohol mixture with 8 to 10 mols of ethylene oxide | 40 gm |
| Perfume oil | 5 gm |
| Dye | 3 gm |
| Keratein | 60 gm |
| Water added to bring the total weight up to | 1000 gm |

A fixing lotion was prepared from the following:

| | |
|---|---|
| Hydrogen peroxide (30%) | 60 gm |
| Condensation product of $C_{12}$ to $C_{18}$ fatty alcohol mixture with 8 to 10 mols of ethylene oxide | 70 gm |

-continued

| | |
|---|---|
| Perfume oil | 5 gm |
| Dye | 3 gm |
| Water added to bring the total weight up to | 1000 gm |

For the hair waving treatment, normal untreated blond hair was saturated at room temperature with the keratein-containing waving lotion and subjected for 30 minutes to the action of the lotion. After treating the hair at room temperature for 10 minutes with the fixing lotion the hair was washed and dried. This treatment was effected 15 times in succession. For comparison, untreated hair was subjected for 30 minutes to a corresponding cold waving lotion, but without addition of keratine; subsequently fixed for 10 minutes; and washed and dried. This treatment was likewise repeated 15 times without the addition of keratein. Testing and comparison of the treated hair showed the following results:

a. Appearance and feel:

The hair treated 15 times with the cold waving lotion without added keratein was almost rubber-like when wet. In the dry state it was hard and brittle. Its appearance was dull.

The hair treated 15 times with the keratein containing cold waving lotion was effected similarly but it was only plastic in the wet state, and softer to feel in the dry state. Moreover the hair had retained its luster.

b. Swelling:

From scanner electron microscopic photographs, a considerable swelling of the hair treated without keratein addition was noticed. But the hair treated with the keratein addition showed greater uniformity and much less swelling.

c. Determination of breaking strength:

The determination of the breaking strength was effected with an extensometer made by Zwick & Co. at 65% relative humidity and 20°C in accordance with DIN 53802. (DIN is the abbreviation for "Deutsche Industrie-Norm" representing a series of standard German published test procedures.) 20 Hairs with an extended length of 50 mm were stretched until breaking occurred. The run-off speed of the extensometer was 60 mm per minute; the advance of the diagram paper was 5:1. The breaking strength is the force necessary to break the hair. The following values were obtained in the measurements, which represent mean values from 10 tests; wherein $\bar{x}$ is the initial hair length.

1. Untreated hair:

Breaking strength = 90.85 pond, elongation in % $\bar{x}$ = 47.0.

2. Hair waved 15 times without the addition of Keratein:

Breaking strength = 31.25 pond, elongation in % $\bar{x}$ = 29.6.

3. Hair waved 15 times with the addition of Keratein:

Breaking strength = 79.4 pond, elongation in % $\bar{x}$ = 48.4.

Thus it can be seen from the foregoing measurements and results that the values for the elongation do not differ substantially between the untreated hair and the hair waved with the addition of keratein. Moreover the breaking strength for the hair waved with the addition of keratein did not fall far below the breaking strength of the untreated hair. But the values of the hair bleached without the addition of keratein indicated considerable damage to the hair in terms of very substantially lesser elongation and very substantially lower breaking strength, both when compared to the untreated hair and when comapred to the hair waved with the addition of keratein.

EXAMPLE 4

Cold Waving Lotion

| | |
|---|---|
| The following substances: | |
| Paraffin oil | 100 parts by weight |
| Fatty alcohol $C_{12}$ to $C_{18}$ mixture | 100 parts by weight, and |
| Condensation product of fatty alcohol $C_{12}$ to $C_{18}$ mixture with 8 to 10 mols ethyleneoxide | 100 parts by weight | are melted together. Then 7600 parts by weight of water at 85° were added to the melt and emulsified. The 600 parts by weight of thioglycolic acid, 900 parts by weight of ammonia (25%) and 600 parts by weight of keratein, produced as described above, were added. The resulting cold waving lotion had a very good waving action without damaging the hair.

EXAMPLE 5

Hair Waving Creme

| | |
|---|---|
| Fatty alcohol $C_{12}$ to $C_{18}$ mixture | 60 parts by weight, and |
| Higher fatty alcohol sulfate | 40 parts by weight | were melted together at 85°C, and the melt was emulsified with 600 parts by weight of water at 85°C. Then the mixture was mixed with 70 parts by weight of thiolactic acid, 100 parts by weight of ammonia (25%) and 50 parts by weight of keratein, produced as described above, and enough water was added to bring the total up to 1000 parts by weight. By using this creme, for waving human hair, the resulting human hair had waves of excellent elasticity. The waved hair had a good luster and hand and showed no sign of damage.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:

1. A preparation for the permanent waving of hair consisting essentially of:
    A. 1% to 10% by weight of keratein,
    B. 3% to 10% by weight of a hair-softening agent and
    C. the balance at least one ingredient selected from the group consisting of a wetting agent, a thickening agent, a pH adjustment reagent, water and mixtures thereof.

2. The preparation of claim 1, wherein the weight of said keratein is 3% to 7% of the weight of said preparation.

3. The preparation of claim 1, wherein the hair-softening agent is selected from the group consisting of a thiolalkanoic acid having from 2 to 6 carbon atoms, a salt of said acid, and mixtures thereof.

4. The preparation of claim 3, wherein said thiolalkanoic acid is selected from the group consisting of thioglycolic acid, thiolactic acid, and mixtures thereof.

5. The preparation of claim 1, wherein the hair-softening agent is a salt of thioglycolic acid.

6. The preparation of claim 1, wherein the hair softening agent is ammonium thioglycolate.

7. In a process for permanent waving hair comprising applying a permanent waving agent containing a hair-softening agent to the hair, at a temperature and for a time effective to permanently wave said hair, applying an oxidizing fixing agent to the hair, and removing said agents from the hair; the improvement which consists essentially in utilizing from 1% to 10% by weight of keratein in said permanent waving agent containing a hair-softening agent.

8. A process for the permanent waving of human hair consisting essentially in applying to said hair at a temperature ranging from about 15°C. to 40°C., for a time sufficient to soften said hair, an effective softening amount of a preparation according to claim 1, applying to said hair carrying said preparation an effective amount of a hair setting agent containing an oxidizing fixing agent, and washing said hair thereby removing said preparation and said fixing agent.

9. The process of claim 8, wherein the hair-softening agent is selected from the group consisting of a thiolalkanoic acid having from 2 to 6 carbon atoms, a salt of said acid, and mixtures thereof.

10. The process of claim 9, wherein said hair softening agent is selected from the group consisting of thioglycolic acid, thiolactic acid, salts of said acids, and mixtures thereof.

11. The process of claim 8 wherein the hair-softening agent is a salt of thioglycolic acid.

12. The process of claim 8, wherein the hair-softening agent is ammonium thioglycolate.

* * * * *